United States Patent
Dijkman et al.

(10) Patent No.: US 10,041,095 B2
(45) Date of Patent: Aug. 7, 2018

(54) PROCESS FOR PRODUCING A MICROBIAL STORAGE COMPOUND

(71) Applicant: Paques I.P. B.V., Balk (NL)

(72) Inventors: Hendrik Dijkman, IJlst (NL); Yang Jiang, Delft (NL); Jelmer Tamis, Delft (NL); Leonie Marang, Den Hoorn (NL); Robbert Kleerebezem, The Hague (NL); Marinus Cornelis Maria Van Loosdrecht, The Hague (NL)

(73) Assignee: PAQUES I.P. B.V., Balk (NL)

( * ) Notice: Subject to any disclaimer, the term of this patent is extended or adjusted under 35 U.S.C. 154(b) by 76 days.

(21) Appl. No.: 15/313,584

(22) PCT Filed: May 22, 2015

(86) PCT No.: PCT/EP2015/061428
§ 371 (c)(1),
(2) Date: Nov. 23, 2016

(87) PCT Pub. No.: WO2015/181083
PCT Pub. Date: Dec. 3, 2015

(65) Prior Publication Data
US 2017/0198314 A1  Jul. 13, 2017

(30) Foreign Application Priority Data
May 26, 2014  (EP) ..................... 14169905

(51) Int. Cl.
*C02F 3/12* (2006.01)
*C02F 3/34* (2006.01)
*C12P 7/62* (2006.01)

(52) U.S. Cl.
CPC ............ *C12P 7/625* (2013.01); *C02F 3/1221* (2013.01); *C02F 3/1263* (2013.01); *C02F 3/34* (2013.01); *C02F 2203/004* (2013.01)

(58) Field of Classification Search
CPC ...... C02F 3/1263; C02F 3/34; C02F 2103/22; C02F 2203/004; C02F 2303/26; C02F 3/1205; C02F 3/121; C02F 3/1221; C02F 3/301; C02F 3/302; C02F 3/308; C02F 2209/10; C02F 2209/21; C02F 3/12; C02F 3/30; C12P 7/625
See application file for complete search history.

(56) References Cited

U.S. PATENT DOCUMENTS

| 8,748,138 B2 * | 6/2014 | Werker | .................. C12P 7/625 435/132 |
| 2013/0029388 A1 * | 1/2013 | Werker | ..................... C02F 3/30 435/135 |

FOREIGN PATENT DOCUMENTS

| WO | WO-00/52189 A1 | 9/2000 |
| WO | WO-2011/031566 A1 | 3/2011 |
| WO | WO-2011/073744 A1 | 6/2011 |
| WO | WO-2012/023114 A1 | 2/2012 |
| WO | WO-2013/022874 A1 | 2/2013 |
| WO | WO-2013/025792 A2 | 2/2013 |
| WO | WO-2014/108864 A1 | 7/2014 |

OTHER PUBLICATIONS

Bengtsson et al., "Production of polyhydroxyalkanoates by activated sludge treating a paper mill wastewater", Bioresource Technology, 2008, vol. 99, pp. 509-516.
Serafim et al., "Strategies for PHA production by mixed cultures and renewable waste materials", Appl Microbiol Biotechnol, 2008, vol. 81, pp. 615-628.
International Search Report issued in International Patent Application No. PCT/EP2015/061428 dated Aug. 7, 2015.

* cited by examiner

*Primary Examiner* — Debbie K Ware
(74) *Attorney, Agent, or Firm* — Gilberto M. Villacorta; Sunit Talapatra; Foley & Lardner LLP (57) ABSTRACT

The invention relates to a process for producing a microbial storage compound, in particular polyhydroxyalkanoate, using micro-organisms capable of accumulating such microbial storage compound, wherein such micro-organisms are selected and the microbial storage compound is accumulated by carrying out the so-called feast phase of the selection step and the accumulation of the microbial storage compound in selected micro-organisms in the same reactor and carrying out the so-called famine phase of the selection step in a separate, smaller, reactor.

18 Claims, 2 Drawing Sheets

PROCESS FOR PRODUCING A MICROBIAL STORAGE COMPOUND

CROSS-REFERENCE TO RELATED APPLICATIONS

This application is the National Phase of International Patent Application No. PCT/EP2015/061428, filed May 22, 2015, published on Dec. 3, 2015 as WO 2015/181083 A1, which claims priority to European Patent Application No. 14169905.8, filed May 26, 2014. The contents of these applications are herein incorporated by reference in their entirety.

FIELD OF THE INVENTION

The invention relates to a process for producing a microbial storage compound, in particular a process for producing polyhydroxyalkanoate (PHA) using micro-organisms accumulating the microbial storage compound.

BACKGROUND

It is known that some micro-organisms that are found in sludge used for aerobic wastewater treatment are able to produce microbial storage compounds, such as for example poly(hydroxyalkanoate) (PHA), as a reserve compound. Recently there is interest in wastewater treatment processes wherein the accumulation of polyhydroxyalkanoate in PHA-accumulating bacteria is maximised in order to recover such polyhydroxyalkanoate from these bacteria, for example for application in bioplastics.

Processes for the selection of micro-organisms capable of producing PHA or other microbial storage compounds are known in the art and typically comprise several cycles alternating a so-called feast phase wherein sludge comprising PHA-accumulating bacteria is fed with a substrate that comprises readily biodegradable organic compounds (so-called readily biodegradable chemical oxygen demand or RBCOD) with a so-called famine phase wherein substrate is withheld from the bacteria. In the feast phase, the PHA-accumulating bacteria are converting RBCOD such as volatile fatty acids into PHA. In the famine phase, the PHA accumulated in the bacteria is used as feed, resulting in selection of those bacteria that are capable of accumulating PHA or other bacterial storage compounds.

For example, WO00/52189 discloses a process for the production of polyhydroxyalkanoate wherein in a first step microorganisms capable of accumulating PHA are selected by alternatingly subjecting the micro-organisms to a phase wherein substrate is added (feast phase) and a phase wherein substrate is withheld (famine phase). In an accumulation step, PHA is accumulated by subjecting some of the micro-organisms selected in the first step to a substrate, preferably a fatty acid-comprising stream. In the process of WO00/52189, the selection step with alternating feast and famine phases is carried out in a first reactor and the accumulation step is carried out in a separate second reactor.

WO2011/073744 also discloses a process for selecting micro-organisms (biomass) capable of producing PHA by alternatingly subjecting biomass to feast and famine conditions. In the process of WO2011/073744, the feast and famine conditions may be applied sequentially in the same reactor, or in separate reactors. Sludge (biomass) withdrawn from the selection process may be subjected to further accumulation in a separate step or to extraction of PHA.

WO2012/023114 discloses a similar process as WO2011073744 for increasing the PHA-accumulating potential of biomass used in the treatment of wastewater by subjecting the biomass to repeated cycles of feast-famine conditions in a Sequencing Batch Reactor (SBR) system, using specific Readily Biodegradable Chemical Oxygen Demand (RBCOD) feeding rates at feast conditions. WO2014/108864, published Jul. 17, 2014, again describes a similar method including a prolonged secondary famine process. In all these methods, any accumulation step is performed in a separate reactor.

WO2013/022874 discloses a process for PHA production using return sludge in an aeration basin in such a manner that a famine-feast regime is provide in the same aeration basin. The return sludge may be treated in a return stream reactor in which a relatively low food-to-biomass ratio is applied. No accumulation is disclosed or suggested.

Serafim et al. *Appl. Microbiol. Biotechnol.* 81 (2008) 615-628 and Bengtsson et al. *Bioresource Technology* 99 (2008) 509-516, disclose processes for the production of PHA using mixed cultures in sequencing batch or continuous reactors, wherein the feast and famine cycles may be performed in a single (selection) reactor. However, the accumulation cycle is always performed in a separate reactor.

SUMMARY OF THE INVENTION

It has now been found that the process for selection of micro-organisms capable of PHA-production or of production of other microbial storage compounds and further accumulation of such microbial storage compound in selected micro-organisms can be improved by carrying out the so-called feast phase of the selection step and the accumulation of the microbial storage compound in selected micro-organisms in the same reactor and carrying out the so-called famine phase of the selection step in a separate reactor.

Accordingly, the invention provides a process for producing a microbial storage compound, comprising the following steps:

a) supplying a stream of wastewater comprising organic compounds including RBCOD to a first reactor containing activated sludge comprising micro-organisms capable of accumulating the microbial storage compound to form a mixture of activated sludge in wastewater and subjecting the sludge in the first reactor to reaction conditions producing (i.e. accumulating) the microbial storage compound, during a first period of time (the "feast phase"), the conditions comprising the presence of dissolved oxygen, to obtain activated sludge comprising the microbial storage compound in treated wastewater;

b) transferring part of the activated sludge comprising the microbial storage compound from the first reactor to a second reactor and retaining part of the activated sludge comprising the microbial storage compound in the first reactor;

c) supplying a stream of wastewater comprising organic compounds including RBCOD to the first reactor containing part of the activated sludge comprising the microbial storage compound to form a mixture of activated sludge comprising the microbial storage compound in wastewater and subjecting the sludge to conditions accumulating the microbial storage compound during a second period of time (the "accumulation phase") to obtain activated sludge that is further enriched in the microbial storage compound and treated wastewater, the accumulating conditions comprising the presence of dissolved oxygen;

d) withdrawing the activated sludge that is further enriched in the microbial storage compound from the first reactor as product stream;

e) subjecting the activated sludge comprising the microbial storage compound in the second reactor in a liquid reaction medium to famine reaction conditions during a third period of time (the "famine phase"), the conditions comprising the presence of dissolved oxygen concentration and a decreased substrate supply, to obtain activated sludge enriched in micro-organisms capable of accumulating the microbial storage compound; and f) transferring the activated sludge enriched in micro-organisms capable of accumulating the microbial storage compound obtained in step e) to the first reactor to form the activated sludge comprising micro-organisms capable of accumulating the microbial storage compound in step a).

An important advantage of a preferred embodiment of the process according to the invention is that the feast phase of the selection step and the accumulation step can be carried out in a continuous reactor, wherein wastewater with substrate is continuously fed to the reactor and treated wastewater may be continuously withdrawn from the reactor, without the typical disadvantages of a continuous process such as a distributed retention time of the biomass (sludge). By discharging the sludge from the first reactor after accumulation step c) and by discharging the sludge from the second reactor after famine phase e), the biomass retention times in each of the steps a), c) and e) are narrowly defined. Thus, the process combines the advantages of a sequencing batch reactor with the advantages of a continuous reactor, i.e. no need to transport large volumes of liquid in a relatively short period of time and therewith no requirement for large pumps and buffer volume capacity. A further advantage is that no separate accumulation reactor is needed.

SUMMARY OF THE DRAWINGS

FIGS. 1 to 7 show a full cycle of the process.

DETAILED DESCRIPTION OF THE INVENTION

The process according to the invention is a process for producing a microbial storage compound. In the process, a stream of wastewater that comprises organic compounds including readily biodegradable chemical oxygen demand (RBCOD) is supplied to a first reactor containing activated sludge comprising micro-organisms capable of accumulating the desired microbial storage compound.

In the context of the present invention the following definitions are applied:

"Microbial storage compounds" are compounds produced by microorganisms such as bacteria, moulds, and algae, for storing their surplus energy. The compounds include esters, polyesters, triglycerides, other fats and oils, and polysaccharides such as glycogen. Polyesters resulting from intermolecular esterification of hydroxycarboxylic acids are an important class of microbial storage compounds, the most prominent ones being poly-hydroxyalkanoic esters, in particular poly-β-hydroxyalkanoic esters, such as poly-β-hydroxybutyrate (PHB) and poly-β-hydroxyvalerate (PHV) having the formulae below, wherein n may range from tens to hundreds or even many thousands, as well as their copolymers.

The poly-hydroxyalkanoic esters (or poly-oxyalkanoates) are commonly (and herein) referred to as polyhydroxyalkanoate (PHA).

"Chemical oxygen Demand" (COD) refers to organic material that can be oxidised to smaller molecules, ultimately to carbon dioxide and water, and the term expresses the amount of oxygen that would be needed to oxidise the organic material in a liter of wastewater.

"Biodegradable COD" refers to organic material in wastewater that can be assimilated for biomass growth.

"Substrate" means substrate for assimilation by microorganisms to allow them to grow, i.e. equivalent to Biodegradable COD.

"Readily Biodegradable Chemical Oxygen Demand (RBCOD)" refers to relatively small organic molecules that can be quickly assimilated by microorganisms as further illustrated below".

"Other Biodegradable Chemical Oxygen Demand (OBCOD)" refers to biodegradable COD other than RBCOD, i.e. more complex and less accessible organic compounds, for example complex polysaccharides, fats and proteins, as well as organic compounds having relatively few oxygen-containing groups and relatively large hydrocarbon groups, such as long-chain fatty acids.

"Wastewater" refers to an aqueous stream comprising COD that needs to be treated before it can be reused or discharged to the environment. The term wastewater for example includes process water, side-product or intermediate product streams from bio-based or other industries, including sugar juices or liquors, municipal wastewater, agricultural wastewater and leaching water of solid biodegradable waste e.g. municipal solid waste and agriculture solid residues.

As defined above, RBCOD refers to relatively simple organic molecules that can be assimilated for growth of micro-organisms and can be quickly taken up and converted into a storage compound, often without requiring hydrolysis. Examples of such RBCOD include volatile fatty acids, also referred to as short-chain fatty acids, i.e. having up to 6 carbon atoms, such as formic acid, acetic acid, propionic acid, butyric acid, isobutyric acid, valeric acid, isovaleric acid, and caproic acid, hydroxy acids such as lactic acid, carbohydrates such as mono-saccharides and disaccharides, uronic acids, alcohols, ketones, and aldehydes, preferably alcohols, ketones, and aldehydes with up to six carbon atoms and combinations of two or more thereof. In other words, RBCOD includes organic compounds having up to 6 carbon atoms per molecule and having at least one hydroxylic (C—OH) or ketonic (C=O) oxygen atom per molecule and at least one oxygen atom per four carbon atoms, preferably having carbon, hydrogen and oxygen atoms only, as well as disaccharides. The concentration of RBCOD can be determined by means of standardised methods of respirometry that determine the fraction of wastewater COD that is rapidly utilised when an aliquot of wastewater with a specified amount of biomass is pulse-fed with substrate under controlled conditions. An example of a suitable standardised method of respirometry is disclosed in M. Henze et al., *Activated Sludge Models ASM1, ASM2, ASM2d and ASM3*, IWA Publishing, London, 2000, p. 16-17; ISBN 1900222248.

The wastewater stream may be batch-wise or continuously supplied to the first reactor in step a). The wastewater stream may be any wastewater stream that comprises RBCOD. Examples of such wastewater streams include municipal, industrial or agricultural wastewater or leaching water of solid biodegradable waste. The stream may be municipal, industrial or agricultural wastewater or process streams or residual streams as such or may be municipal, industrial or agricultural wastewater that has been pre-treated, for example has been pre-hydrolysed to convert so-called OBCOD to RBCOD, and/or has been pre-acidified or fermented to convert saccharides or other compounds to carboxylic acids, preferably volatile fatty acids or lactic acid. Thus, the process of the invention may comprise a preceding step in which the raw wastewater is subjected to hydrolysis and/or fermentation in a separated reactor, for example an anaerobic formation reactor in which the partial fermentation (hydrolysis, acidogenesis, acetogenesis) is achieved.

The stream of wastewater supplied to the first reactor in step a) may further comprise OBCOD. Preferably, the stream of wastewater comprises more RBCOD than OBCOD. Preferably, the stream of wastewater comprises RBCOD in the range of from 0.5 to 50 grams per liter, more preferably in the range of from 1 to 20 grams per liter. The stream of wastewater preferably comprises volatile fatty acids, more preferably in the range of from 0.5 to 50 grams per liter volatile fatty acids, even more preferably in the range of from 1 to 20 grams per liter.

The activated sludge comprises micro-organisms that are capable of producing the desired microbial storage compound. Preferably, the microbial storage compound is PHA and the process is a process for producing PHA. In that case, the activated sludge comprises PHA-accumulating micro-organisms, preferably PHA-accumulating bacteria. Once the process operates in steady state, the activated sludge is the activated sludge that is further enriched in accumulating micro-organisms obtained in famine step e) and transferred to the first reactor in step f). At the start of the process, the first reactor may be inoculated with activated sludge or other samples comprising such accumulating micro-organisms or with strains of micro-organisms capable of accumulating the desired microbial storage compound, in particular PHA. In case the stream of wastewater supplied to the first reactor comprises micro-organisms capable of accumulating the desired microbial storage compound, the process may be started without inoculating the first reactor with sludge or with such micro-organisms.

PHA-accumulating bacteria and other micro-organisms capable of accumulating microbial storage compounds are typically present in non-axenic cultures of micro-organisms such as are found in soil, natural water or mixed biomass samples. They can also be isolated or enriched from common municipal wastewater plants. The PHA-accumulating bacteria can belong to various genera such as *Alcaligenes* (e.g. *A. latus*), *Ralstonia* (e.g. *R. eutropha*), *Cupriavidus* (e.g. *C. necator*), *Chromatium* (e.g. *C. vinosum*) *Mycobacterium, Bacillus, Pseudomonas*, etc. They may specifically or non-specifically grow on various carbon sources such as glucose, methanol, ethanol, acetate and/or other fatty acids. See e.g. Tan G-Y. A. et al. Polymers 2014, 6, 706-754; Huang Y-T. et al. *J. Microbiol. Biotechnol.* 2012, 22, 1141-47. Particularly useful are bacteria of the genus *Plasticicumulans*, such as *P. acidivorans* (acetate-consuming) and *P. lacatativorans* (lactate-consuming), see e.g. Tamis J. et al. *J. Biotechnology* 2014, 192, 161-169.

By supplying wastewater to the first reactor in step a), a mixture of activated sludge in wastewater is formed in the first reactor and the mixture is then subjected to reactions conditions accumulating microbial reserve compound, in particular PHA-accumulating reaction conditions, during a first period of time to obtain activated sludge comprising the microbial storage compound in treated wastewater. The period of time applies to the mixture in case of batch operation. If the wastewater is intermittently or continuously added (and hence treated waste water is intermittently or continuously discharged), the period of time applies to the retention time of the sludge, which is not discharged together with the (continuously) discharged treated wastewater, or to the average retention time in case of (semi) continuous sludge exchange.

The reaction conditions producing the microbial reserve compound, in particular the PHA-producing reaction conditions are so-called feast conditions and comprise the presence of substrate in the form of RBCOD and the presence of dissolved oxygen. Where reference is made herein to dissolved oxygen, this means dissolved molecular oxygen unless stated otherwise. In order to have dissolved oxygen, preferably a molecular-oxygen-comprising gas, more preferably air, is supplied to the first reactor. This may be done continuously or discontinuously, preferably continuously, during step a).

The amounts of RBCOD and of dissolved oxygen are such that they are not limiting for the production of the microbial storage compound. It will be appreciated that the minimum concentrations of RBCOD and dissolved oxygen will depend on the amount of micro-organisms capable of accumulating microbial storage compound present in the reactor, the microbial storage compound to be produced and other process conditions such as temperature and pH of the mixture in the reactor. Preferably, the dissolved oxygen concentration will be at least 0.32 mg, more preferably at least 0.5 mg $O_2$ per liter. The concentration of RBCOD will preferably be at least 10 mg/L.

In case the microbial storage compound is PHA and the process is a process for producing PHA, the PHA-accumulating reaction conditions in step a) preferably comprise a pH in the range of from 4 to 10, more preferably of from 6 to 8, a temperature in the range of from 10 to 50° C., more preferably of from 20 to 40° C., and a conductivity in the range of from 0 to 20 mS/cm.

During feast step a), the micro-organisms capable of accumulating the microbial storage compound produce the microbial storage compound by converting RBCOD to the microbial storage compound. The microbial storage compound thus formed is stored in the micro-organisms, typically in the form of granules. Thus, activated sludge comprising the microbial storage compound is formed in the treated wastewater. The microbial storage compound accumulating reaction conditions in step a) are maintained during a first period of time. The first period of time may be a pre-determined period of time, preferably a pre-determined period of time in the range of from 0.25 to 5 hours, more preferably in the range of from 0.5 to 2 hours. Alternatively, the first period of time ends when a certain minimum concentration of RBCOD is achieved (in case of batch supply of wastewater and therewith of substrate), when a certain amount of the microbial storage compound is produced, or when the oxygen consumption decreases. Alternatively, the RBCOD concentration in the mixture in the first reactor during step a) may be kept constant by adjusting the supply of the stream of wastewater. The first period of time may then end when the flow rate of wastewater supply drops below a certain value.

In case the microbial storage compound is PHA, the first period of time is preferably such that the PHA-accumulating bacteria in the activated sludge have, at the end of step a), accumulated at least 30 wt. % of PHA, based on the dry weight of sludge, for example 30 to 50 wt %, or even at least 50% of PHA, up to e.g. 80 wt. % of PHA. Preferably the first period of time, whether pre-determined or not, is in the range of from 0.25 to 5 hours, more preferably in the range of from 0.25 to 2 hours or even from 0.5 to 2 hours. In case waste water is semi-continuously or continuously fed to the first reactor in the feast phase, the periods of time refer to the (average) retention times of the sludge, not of the wastewater.

After the first period of time, i.e. after the feast phase, part of the activated sludge comprising the microbial storage compound is transferred from the first reactor to a second reactor and part of the activated sludge comprising the microbial storage compound is retained in the first reactor (step b)). This may be done by transferring part of the mixture of activated sludge and treated waste water that is contained in the first reactor to the second reactor at the end of step a). Preferably, the mixture contained in the first reactor at the end of step a) is concentrated in solids, i.e. in activated sludge comprising the microbial storage compound, prior to being transferred to the second reactor. The concentration of solids is preferably a factor two or more, more preferably a factor four or more. Such concentration may be done by means known in the art, for example by means of sedimentation of sludge inside or outside the first reactor or by means of a solid-liquid separator inside or outside the first reactor. Suitable solid-liquid separators are known in the art and include settlers, hydrocyclones, centrifuges, membranes and belt filters. Preferably, such concentration is carried out in a settler inside the first reactor, more preferably by means of sedimentation. Such sedimentation can be achieved by stopping the supply of wastewater and of air to the first reactor at the end of step a).

An advantage of concentrating the activated sludge before transferring such sludge to the second reactor is that a smaller second reactor can be used. Since the famine phase carried out in the second reactor in step e) can be operated at a higher solid (sludge) to liquid ratio than the first reactor in step a), it is advantageous to selectively transfer sludge to the second reactor. A further advantage of transferring less of the liquid phase from the first reactor to the second reactor is that less OBCOD is transferred to the second reactor, thus minimising the growth of undesired side populations, i.e. unwanted OBCOD-oxidising biomass. Moreover, since the desired biomass accumulating storage compound is heavier than the undesired biomass, concentration of activated sludge before transfer of such sludge to the second reactor can advantageously be carried out such that undesired biomass is separated from the desired accumulating micro-organisms in the activated sludge to be transferred.

Preferably, part of the treated wastewater is transferred from the first reactor to the second reactor, typically with the (concentrated) mixture of sludge and treated wastewater, to serve as liquid reaction medium in famine step e). Alternatively, treated wastewater may be first separated from the solid sludge in an internal or external separator and then part of the separated treated wastewater may be transferred to the second reactor to serve as liquid reaction medium in famine step e). In some situations, for example in case the stream of wastewater has a relatively high salt concentration and the famine phase in the second reactor (step e)) is preferably operated at a lower salt concentration, no or a minimum amount of treated wastewater is transferred to the second reactor and a fresh aqueous liquid is supplied to the second reactor to serve as liquid reaction medium in famine step e).

Part of the activated sludge comprising the microbial storage compound is retained in the first reactor. Preferably, at least 30 wt % of the sludge is retained in the first reactor after step a), more preferably in the range of from 40 to 60 wt %. The remainder, preferably at least 30 wt % up to 70 wt %, more preferably 40-60 wt % is transferred to the second reactor.

Preferably, a substantial amount of treated wastewater is retained in the first reactor after step a) and during step b) so that no large buffer volume of liquid is needed for filling the first reactor at the start of accumulation step c).

In step c), a stream of wastewater comprising organic compounds including RBCOD is supplied to the first reactor wherein part of the activated sludge comprising the microbial storage compound is retained to form a mixture of such activated sludge in wastewater. This mixture is then subjected to microbial storage compound accumulating conditions during a second period of time (the accumulation phase). Under these conditions, the accumulating micro-organisms in the sludge convert RBCOD into the microbial storage compound, therewith further accumulating the microbial storage compound. Activated sludge further enriched in the microbial storage compound is thus obtained. Again, in a (semi)-continuous mode, i.e. if the wastewater is intermittently or continuously added, the period of time does not apply to the mixture as such, but to the sludge, which is not discharged together with the (continuously) discharged treated wastewater; this means that the period of time refers to the (average) retention time of the sludge.

The accumulating conditions comprise the presence of RBCOD and the presence of dissolved oxygen. The amounts of RBCOD and of dissolved oxygen in the mixture in the first reactor in accumulating step c) are such that they are not limiting for the accumulation of the microbial storage compound. It will be appreciated that the minimum concentrations of RBCOD and dissolved oxygen will depend on the amount of accumulating micro-organisms present in the reactor, the microbial storage compound to be produced and other process conditions such as temperature and pH of the mixture in the reactor. Preferably, the dissolved oxygen concentration will be at least 0.5 mg $O_2$ per liter. The concentration of RBCOD will preferably be at least 10 mg/L. In case the microbial storage compound is PHA and the process is a process for producing PHA, the PHA-accumulating reaction conditions in step c) preferably comprise a pH in the range of from 4 to 10, more preferably of from 6 to 8, a temperature in the range of from 10 to 50° C., more preferably of from 20 to 40° C., and a conductivity in the range of from 0 to 20 mS/cm.

The accumulating conditions are preferably the same as the reaction conditions accumulating microbial storage compound in step a). In order to minimise growth during feast (step a) and accumulation (step c), the wastewater fed to the first reactor is preferably limited in one or more nutrients, for example limited in nitrogen (ratio biodegradable COD to N more than 300 to 1 based on weight) or limited in phosphorus (ratio biodegradable COD to P more than 1500 to 1 based on weight).

Preferably, the stream of wastewater that is supplied to the first reactor in accumulation step c) is the same as the stream of wastewater supplied to the first reactor in feast step a). In a preferred embodiment, the continuous supply of molecular oxygen and of wastewater to the first reactor is temporarily stopped after step a) to allow the activated sludge comprising the microbial storage compound to sediment in the first reactor. A part of the sedimented sludge is then transferred to the second reactor in step b), typically together with some of the treated wastewater. The supply of molecular oxygen and wastewater to the first reactor is then resumed to start accumulation step c). In such embodiment with continuous supply of wastewater and molecular oxygen to the first reactor, the flow rates of the supply of oxygen and wastewater may be varied during the runtime of steps a) and c).

Step c) is carried out during a second period of time. The second period of time may be a pre-determined period of time, preferably a pre-determined period of time in the range of from 2 to 24 hours, more preferably in the range of from 4 to 24 hours or even from 4 to 12 hours. Alternatively, the second period of time ends when a certain minimum concentration of RBCOD is achieved (in case of batch supply of wastewater and therewith of substrate) when a certain amount of microbial storage compound is produced, or when the oxygen consumption decreases. Alternatively, the RBCOD concentration in the mixture in the first reactor during step c) may be kept constant by controlling the supply of the stream of wastewater. The second period of time may then end when the flow rate of wastewater supply drops below a certain value. The second period of time, i.e. the length of the accumulation phase, is preferably longer than the first period of time, i.e. the feast phase. In particular, the second period of time is at least two times, up to e.g. 24 times as long as the first period of time, more in particular, between 4 and 20 times as long.

In case the microbial storage compound is PHA, the second period of time is preferably such that the PHA-accumulating bacteria in the activated sludge have, at the end of step c), accumulated at least 60 wt %, more preferably at least 70 wt %, even more preferably at least 80 wt % of PHA, up to e.g. 90 wt. % of PHA, based on the dry weight of sludge.

Treated wastewater may be continuously withdrawn from the first reactor during steps a) and/or c) or batch-wise at the end of step a) or during step b). In case treated wastewater is continuously withdrawn from the first reactor during steps a) and/or c), the first reactor preferably comprises a settler for separating any sludge from the treated wastewater so that sludge is retained in the first reactor. Such settler may be located inside the reactor, preferably in an upper part of the reactor just before an outlet for treated wastewater, or outside the reactor with recycling of separated sludge to the first reactor. It will be appreciated that a settler for preventing sludge to be withdrawn from the first reactor with the continuous withdrawal of treated wastewater is a different settler as a settler that may be used to concentrate activated sludge that is to be transferred to the second reactor in step b).

At the end of accumulation step c), i.e. after the second period of time, the activated sludge that is further enriched in the microbial storage compound is withdrawn from the first reactor as product stream in step d). Microbial storage compound may be recovered from this product stream in one or more further steps for application in for example bioplastics. Such steps are well-known in the art and typically comprise disruption of the microbial cells to harvest the microbial storage compound and further purification steps.

In step e), the activated sludge comprising the microbial storage compound in the second reactor is subjected in a liquid reaction medium, typically in a liquid reaction medium of treated wastewater from the first reactor, to so-called famine conditions during a third period of time to obtain activated sludge enriched in micro-organisms capable of accumulating the microbial storage compound. The famine conditions comprise the presence of dissolved oxygen and the absence of substrate supply, i.e. without added BCOD, or the presence of substrate at a lower average level than during the feast phase of step a) in that, during step e), the RBCOD supply is substantially lower than the rate of uptake by the microorganisms. Thus, step e) involves a depletion of RBCOD, meaning that RBCOD concentration is reacted away by the microorganisms accumulating the storage compound (such as PHA), at which stage the microorganisms start using the storage compound for growth. In particular, the supply of substrate is substantially zero. Undesired microorganisms can grow in the famine phase by consuming the OBCOD present. This is why OBCOD supply should preferably be minimised as described above.

Such famine conditions are well-known in the art and any suitable famine conditions known in the art may be applied. In famine step e), the concentration of biodegradable COD (RBCOD and OBCOD) in the liquid reaction medium is preferably less than 0.1 times, more preferably less than 0.02 times, the concentration of biodegradable COD in feast step a); i.e. it reaches these lower levels at an early stage of famine step e). In particular, the concentration of RBCOD alone in the liquid reaction medium of step e) preferably reaches less than 0.1 times, more preferably less than 0.02 times, the concentration of RBCOD in feast step a). The concentration of dissolved oxygen is preferably such that it is not limiting for the growth of the micro-organisms capable of accumulating the microbial storage compound. Preferably, the concentration of dissolved oxygen in the second reactor in step e) is at least 0.32 mg, more preferably at least 0.5 mg per liter liquid reaction medium.

Since step e) is the step wherein growth of the desired micro-organisms takes place, it is important that nutrients essential for such growth are present in the liquid reaction medium. In case the concentration of essential nutrients is limiting for growth of such micro-organisms in the treated wastewater that is transferred from the first reactor to the second reactor, it is preferred to add such nutrients to the second reactor just before or during step e). Nutrients that may be added comprise a source of P, such as phosphate, a source of N, such as ammonia, ammonium, urea or nitrate, other macro elements or trace elements, or combinations thereof.

After step e), the activated sludge enriched in micro-organisms capable of accumulating the microbial storage compound is withdrawn from the second reactor and transferred to the first reactor to form the activated sludge comprising micro-organisms capable of accumulating the microbial storage compound in step a).

The third period of time preferably is a pre-determined period of time, more preferably a pre-determined period of time in the range of from 2 to 24 hours, more preferably 4 to 24 hours, even more preferably in the range of from 4 to 12 hours. It applies in particular to the retention time of the sludge in the second reactor or average retention time in case of (semi)continuous sludge exchange.

In a preferred embodiment of the invention, accumulation step c) and famine step e) are carried out simultaneously and preferably have a comparable length, i.e. the second and third reaction time are about the same. Thus, the third period of time is preferably at least two times, up to e.g. 24 times as long as the first period of time, more in particular, between 4 and 20 times as long. In case it is desired to have a third period of time (famine phase) that is substantially longer than the second period of time (accumulation step), it is preferred to operate the process according to the invention with more than one second reactors, preferably with two second reactors. In case of two second reactors, activated sludge that has been enriched in the desired accumulating micro-organisms in a famine phase (step e)) that uses activated sludge obtained in the feast phase (step a)) of a previous cycle of the process, is then transferred to the first reactor in step f). In this way, the residence time in each second reactor may be as long a two times the second period of time plus one time the first period of time. Thus, the residence time in the famine phase is then about two times the residence time in the accumulation step, and may up to 40 times the length of the first period of time (feast phase).

At the end of accumulation step c), the activated sludge is withdrawn from the first reactor as a product stream (step d)). Preferably, essentially all activated sludge is withdrawn from the first reactor in step d). Preferably, the activated sludge is selectively withdrawn from the first reactor, i.e. with retaining most of the liquid phase in the reactor. An advantage of selective withdrawal of sludge is that less pumping and buffer liquid would be needed. Such selective withdrawal may be done by means known in the art, for example by first allowing the sludge to sediment in the first reactor before withdrawing the sedimented sludge. Alternatively, a suitable solid/liquid separator inside or outside the first reactor may be used, such as a settler, a centrifuge, a hydrocyclone, a filter or a membrane. If the solid/liquid separation takes place outside the first reactor, this is preferably done in a recycle loop and most of the separated liquid is recycled to the first reactor.

By aligning the residence times of the accumulation step in the first reactor and the famine phase in the second reactor, optimum use is made of the first and the second reactor. Moreover, by carrying out the famine step in a different reactor than the feast and accumulation steps, the reactor dimensioning can be optimised, since the requirements for the feast phase and the accumulation step in terms of oxygen and substrate supply are comparable, whereas those for the famine phase are different. Thus, over-dimensioning of the reactor, which is usually the case in the prior art processes wherein the feast and famine phases are carried out in a single reactor, is avoided.

The desired dissolved oxygen concentrations in steps a) and c) in the first reactor and in step e) in the second reactor are maintained by supplying molecular oxygen or another oxygen-comprising oxidant to the first reactor or the second reactor during these steps, preferably by continuously feeding a stream of air to the relevant reactor.

The volume of the second reactor is typically smaller than the volume of the first reactor. Preferably, the volume of the second reactor is from 5% to at most 50% of the volume of the first reactor, more preferably in the range of from 10% to 20% of the volume of the first reactor. This is mainly due to the fact in step e) (famine phase) a larger sludge to liquid reaction medium ratio may be used than in steps a) and c) in the first reactor. Preferably, the ratio of sludge to liquid reaction medium in step e) is in the range of 2 to 10 times larger than in steps a) and c), more preferably in the range of from 5 to 8 times larger.

In a preferred embodiment of the process of the invention, steps a) and c) are performed batch-wise or continuously with respect to feeding wastewater, and steps b), d) and f) are performed batch-wise with respect to transferring sludge, i.e. after completion of the first, second, and third period of time, respectively, as further explained above. In another embodiment of the invention, one or more of steps b), d) and f), preferably at least steps b) and f), are performed continuously or semi-continuously (intermittently), i.e. during steps a), c) and e), respectively. In such a fully continuous mode, the first, second and third periods of time for subjecting the various sludges to the feast, accumulation and famine conditions, respectively, apply to the average sludge retention times in the first reactor and in the second reactor; (these are the times before the sludge is returned to the second reactor (step a)) and before the product sludge is discharged from the first reactor (step c)) and before the grown sludge is returned to the first reactor (step e)).

DETAILED DESCRIPTION OF THE DRAWINGS

FIGS. 1 to 7 schematically show different sequential steps of an embodiment of the process according to the invention. Together FIGS. 1 to 7 show a full cycle of the process.

Equal reference numbers in the Figures have the same meaning. Dotted lines show conduits through which no stream is flowing, normal lines show conduits through which a stream is flowing during the depicted step of the process.

Figure 1:
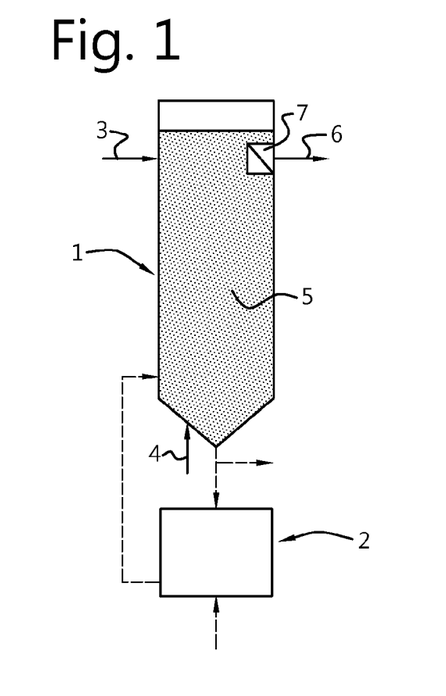
FIGS. 1 to 7 schematically show the first and the second reactor and solid and fluid streams in sequential steps of an embodiment of the process according to the invention. Together

FIG. 1 represents the so-called feast phase (step a)) of the process according to the invention. In FIG. 1 is shown first reactor 1, and second reactor 2. A stream of wastewater comprising volatile fatty acids is continuously supplied to first reactor 1 with conduit 3 and air is continuously supplied to first reactor 1 with conduit 4. First reactor 1 contains a mixture 5 of activated sludge comprising PHA-accumulating bacteria dispersed in (treated) wastewater. The reactor is operated under so-called feast conditions (PHA-producing reaction conditions). Under these conditions, volatile fatty acids are converted into PHA by the PHA-accumulating bacteria in the activated sludge. Thus, PHA-comprising activated sludge is obtained. Treated wastewater is continuously withdrawn from reactor 1 via conduit 6. Settler 7 separates sludge from the treated wastewater and therewith the sludge is retained in first reactor 1.

Figure 2:
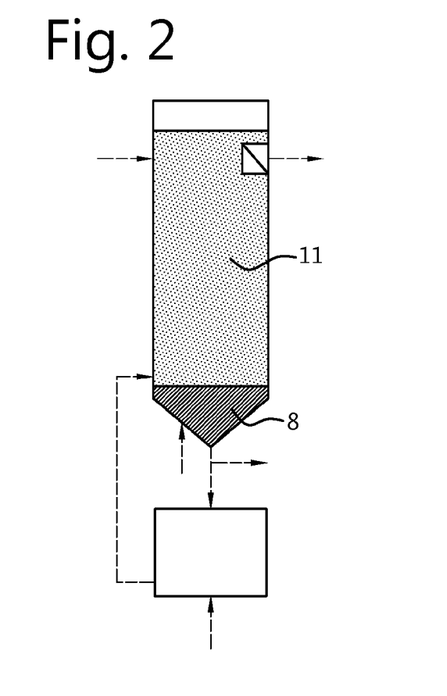

FIG. 2 shows the subsequent sedimentation step in the process. By interrupting the supplies of wastewater and air via conduits 3 and 4, respectively, the PHA-comprising activated sludge is allowed to sediment, and a layer 8 of concentrated PHA-comprising activated sludge is formed. Above layer 8, a more diluted mixture 11 of PHA-comprising activated sludge dispersed in treated wastewater is present.

Figure 3:
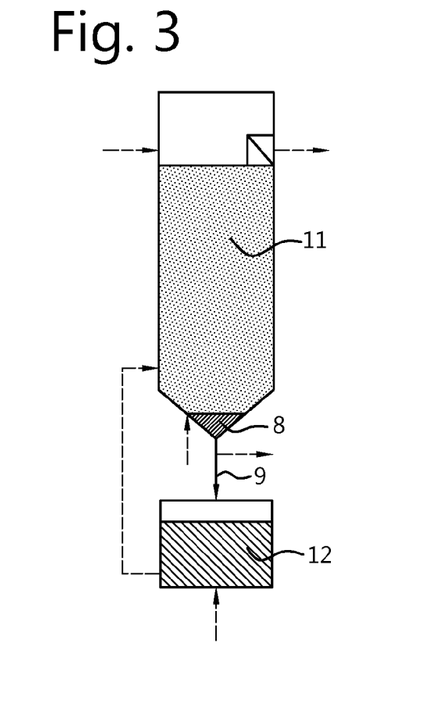

FIG. 3 shows the subsequent step b) of the process wherein concentrated PHA-comprising activated sludge is transferred via conduit 9 to second reactor 2 (approximately half of layer 8 is transferred to second reactor 2). Second reactor 2 now contains a concentrated mixture 12 of PHA-comprising activated sludge in treated wastewater.

Figure 4:
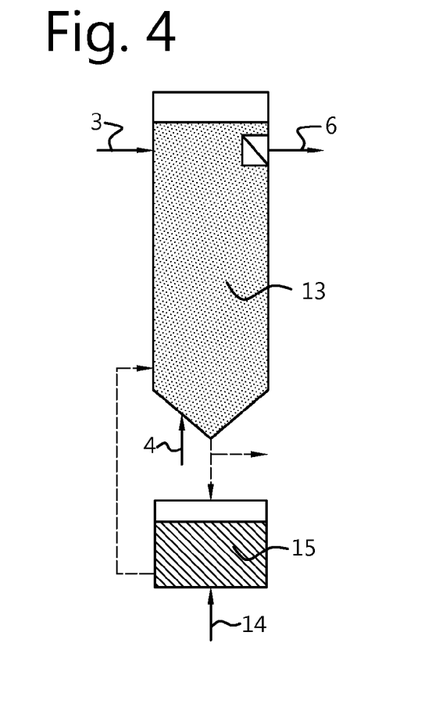

FIG. 4 shows subsequent accumulation step c) in first reactor 1 and famine step e) in second reactor 2. Steps c) and e) are carried out simultaneously. The supplies of wastewater and air to first reactor 1 via conduits 3 and 4 are resumed and treated wastewater is continuously withdrawn from reactor 1 via line 6. The conditions during step c) are essentially the same as in step a). During step c) PHA is further accumulated in the PHA-accumulating bacteria and a mixture 13 of activated sludge further enriched in PHA dispersed in treated wastewater is obtained.

In simultaneous step e), air is supplied to second reactor 2 via conduit 14. No substrate is supplied to second reactor 2. Under these so-called famine conditions, i.e. under conditions that the concentration of substrate is limiting, the bacteria that have produced and stored PHA in step a) selectively grow and activated sludge 15 further enriched in PHA-accumulating bacteria is obtained.

Figure 5:
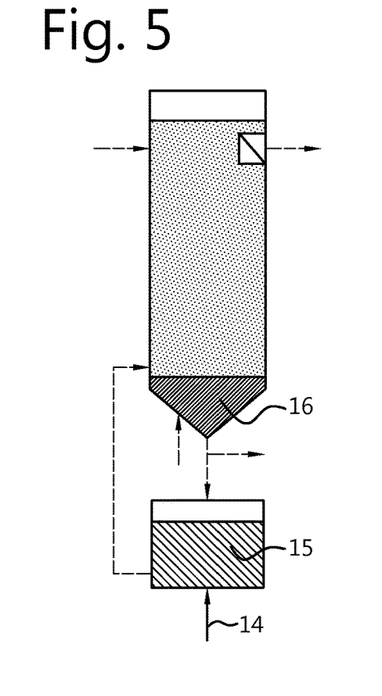

FIG. 5 shows the subsequent sedimentation step in the process. By interrupting the supplies of wastewater and air via conduits 3 and 4, respectively, the activated sludge further enriched in PHA in first reactor 1 is allowed to sediment, and a layer 16 of concentrated sludge further enriched in PHA is formed.

Figure 6:
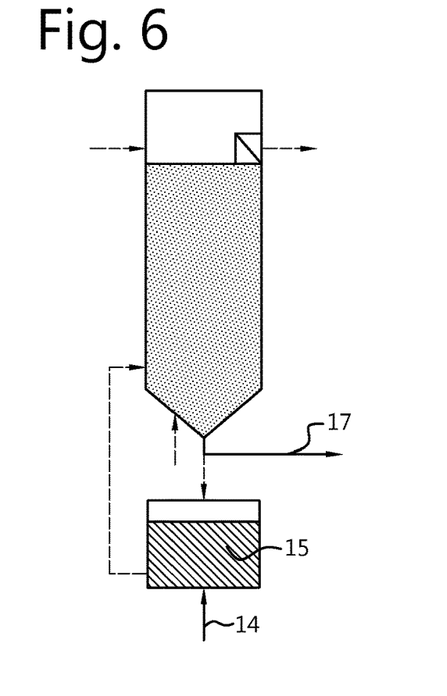

FIG. 6 shows subsequent step d) wherein the concentrated sludge further enriched in PHA is withdrawn from first reactor 1 via conduit 17 as product stream.

Figure 7:
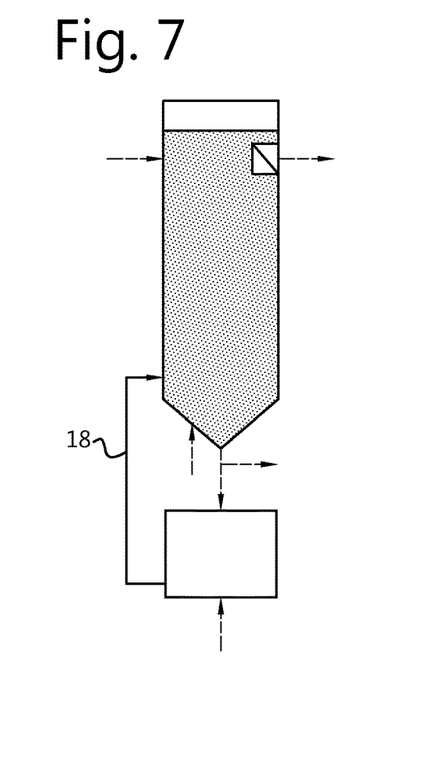

FIG. 7 shows subsequent step f) wherein activated sludge further enriched in PHA-accumulating bacteria is transferred via conduit 18 from second reactor 2 to first reactor 1 to form the activated sludge comprising PHA-accumulating bacteria to be used in subsequent step a), i.e. the first step of a subsequent cycle of the process. By repeating the cycles of the process as shown in FIGS. 1 to 7, a selection pressure for PHA-accumulating bacteria is achieved.

EXAMPLES

Conversion of RBCOD present in waste water to biomass with a high PHA content which thereafter can be further purified requires two steps:

Firstly, an efficient selection process is required in order to produce the required amount of biomass with an as high as possible content of the desired PHA-accumulating bacteria. This is typically done in a Feast-Famine regime where bacteria in a short time convert RBCOD to PHA and in longer time grow by converting the PHA to biomass. The Famine time is typically more than 10 times longer than the Feast time.

Secondly, this biomass needs to be contacted with a high amount of RBCOD-containing waste water in order to maximise the PHA content in the cells (Accumulation step).

In order to produce biomass containing about 85 wt % PHA, around 20% of the RBCOD-containing wastewater is used for biomass production and about 80% for PHA production in the Accumulation step.

The prior art considers the Selection and Accumulation as separate steps. The present invention shows the advantages of an integrated system where Selection and Accumulation are combined.

Example (Comparative)

This example shows estimated Bioreactor sizing using a separate Selection (Feast-Famine) Sequencing Batch Reactor (SBR) and a separate Accumulation reactor compared to a combined Feast/Accumulation reactor and a separate Famine reactor assuming max. 1 kg/m3·h oxygen transferred for all reactors. The oxygen requirement in the Feast and Accumulation phase is found to be around 0.3 kg $O_2$ per kg acetate converted to PHA. The absolute amount of oxygen required in the Famine phase is comparable with the Feast phase but as the Famine time is more than 10 times longer than the Feast phase the required oxygen transfer rate is more than 10 times smaller in case the same reactor volume is used for the Feast and the Famine phases as is the case for the SBR set-up. The required oxygen transfer rate in the Feast phase therefore determines the reactor volume in case oxygen transfer is limiting. This will normally be the case at elevated RBCOD concentrations.

Total Waste Water Available:
RBCOD concentration: 4 g/l (kg/m$^3$) acetate
Time-averaged wastewater flow: 100 m$^3$/h
   Selection in One (Feast-Famine) Sequencing Batch Reactor:
Time-averaged wastewater flow to Selection: 20 m$^3$/h
Time-averaged acetate load: 20×4=80 kg/h
Feast+Famine cycle: 12 h, of which Feast time: 40 minutes (0.667 h) and
Famine time: 11 h 20 m (11.333 h)
Acetate uptake during Feast phase only: 80×12 h/0.667 h=1440 kg/h acetate.
Oxygen requirement in the Feast phase=1440×0.3=432 kg/h $O_2$.
Reactor volume based on max. of 1 kg/m$^3$·h and average 1 kg/m$^3$·h $O_2$ transfer rate=432 kg/h: 1 kg/m$^3$·h=432 m$^3$.
   Accumulation Reactor:
Time-averaged wastewater to Accumulation: 80 m$^3$/h.
Time-averaged acetate load: 80×4=320 kg/h acetate.
Time averaged oxygen requirement in the Accumulation reactor=320×0.3=96 kg/h $O_2$.
Volume based on max. of 1 kg/m$^3$·h $O_2$ and average 0.5 kg/m$^3$·h $O_2$ transfer rate=96/0.5=192 m$^3$. →total reactor capacity required: 432+192=624 m$^3$
   Main disadvantages of this set-up:
   the available oxygen transfer capacity in the Selection reactor is only used for around 5 to 10% of the time during the Feast phase. For the rest of the time more than 90% of the oxidation capacity is not used.
   in case settling after Feast is applied in order to remove OBCOD, the reactor will be operated more than half empty for more than 90% of the time. Beside the lower efficiency this also presents technical problems for selecting aeration devices.
   every cycle in the Selection 12 h×20 m$^3$/h=240 m$^3$ water needs to be stored and pumped in short time at the beginning and the end of the cycle.

Example (Invention)

It was found according to the invention that these problems can be overcome by using the same volume first reactor also for Accumulation and applying a smaller Famine reactor instead of a separate Accumulation reactor.
   Combined Feast and Accumulation reactor:
Time-averaged wastewater to Selection: 100 m$^3$/h
Time-averaged acetate load: 100×4=400 kg/h
Time-averaged oxygen requirement=400×0.3=120 kg/h $O_2$
Volume based on max. of 1 kg/m$^3$·h $O_2$ and average 0.277 kg/m$^3$·h $O_2$ transfer rate=120/0.277=433 m$^3$.
   Famine Reactor
The separate famine reactor can be 10 times smaller compared to the first reactor as a result of the lower oxygen requirement and by minimising the hydraulic flow rate due to sludge thickening after the Feast phase: 45 m$^3$.
→ total reactor capacity required: 436+45=481 m$^3$
Besides lower overall reactor volume and more efficient use of installed aeration capacity and energy, also less hydraulic wastewater buffer capacity is required as the total amount of water pumped in short time from the second to the first reactor is less than 45 m$^3$ per cycle.

The invention claimed is:

1. A process for producing polyhydroxyalkanoate (PHA), comprising:
    (a) supplying a stream of wastewater comprising Readily Biodegradable COD (RBCOD) to a first reactor containing activated sludge comprising micro-organisms capable of accumulating PHA;

(b) subjecting the sludge in the first reactor to PHA-accumulating reaction conditions during a first period of time from 0.25 to 5 h, the conditions comprising the presence of dissolved oxygen and the presence of at least 10 mg/l readily biodegradable COD in the mixture, to obtain activated sludge comprising PHA at a level of at least 30 wt. % based on the dry weight of the sludge;

(c) transferring part of the activated sludge comprising PHA from the first reactor to a second reactor and retaining part of the activated sludge comprising PHA in the first reactor;

(d) supplying a stream of wastewater comprising RBCOD to the first reactor containing part of the activated sludge comprising PHA and subjecting the sludge to PHA-accumulating conditions during a second period of time from 2 to 24 h, the PHA-accumulating conditions comprising the presence of dissolved oxygen and the presence of at least 10 mg/l readily biodegradable COD, to obtain activated sludge that is further enriched in PHA to a level of at least 60 wt. % based on the dry weight of the sludge, and treated wastewater;

(e) withdrawing the activated sludge that is further enriched in PHA from the first reactor as a product stream;

(f) subjecting the activated sludge comprising PHA in the second reactor in a liquid reaction medium to famine reaction conditions during a third period of time of between 2 and 24 h, the famine reaction conditions comprising the presence of dissolved oxygen, to obtain activated sludge enriched in micro-organisms capable of accumulating PHA; and (g) transferring the activated sludge enriched in micro-organisms capable of accumulating PHA obtained in step (f) to the first reactor to form the activated sludge comprising micro-organisms capable of accumulating PHA in step a).

2. The process according to claim 1, wherein the micro-organisms are bacteria.

3. The process according to claim 1, wherein the concentration of readily biodegradable COD in the stream of wastewater is between 0.5 to 50 grams per liter.

4. The process according to claim 3, wherein the concentration of readily biodegradable COD in the stream of wastewater is between 1 to 20 grams per liter.

5. The process according to claim 4, wherein the stream of wastewater comprises volatile fatty acids.

6. The process according to claim 5, wherein the concentration of the volatile fatty acids is in the range of from 0.5 to 50 grams per liter.

7. The process according to claim 6, wherein the concentration of the volatile fatty acids is in the range of from 1 to 20 grams per liter.

8. The process according to claim 1, wherein steps (d) and (f) are carried out simultaneously.

9. The process according to claim 1, wherein the first period of time in step (b) is in the range of from 0.5 to 2 hours.

10. The process according to claim 1, wherein the second period of time in step (d) is in the range of from 4 to 12 hours.

11. The process according to claim 1, wherein third period of time in step (f) is from 4 to 12 h.

12. The process according to claim 1, wherein the stream of wastewater is continuously supplied to the first reactor during steps (a) and (d) and a stream of treated wastewater is continuously withdrawn from the first reactor during steps (a) and (d).

13. The process according to claim 1, wherein steps (c), (e) and (g) are performed after completion of the first, second, and third period of time, respectively.

14. The process according to claim 1, wherein one or more of steps (c), (e) and (g) are performed continuously.

15. The process according to claim 1, wherein in step (c), the transferred part is at least 40 wt % and the retained part is at least 30% of the activated sludge comprising PHA.

16. The process according to claim 1, wherein the part of the activated sludge comprising PHA transferred from the first reactor to the second reactor in step (c) is concentrated prior to being supplied to the second reactor.

17. The process according to claim 16, wherein the part of the activated sludge comprising PHA transferred from the first reactor to the second reactor is concentrated in the first reactor prior to being withdrawn from the first reactor.

18. The process according to claim 1, wherein the volume of the second reactor is 50% or less of the volume of the first reactor.

* * * * *